United States Patent [19]

Viera

[11] Patent Number: 5,353,808
[45] Date of Patent: Oct. 11, 1994

[54] GUIDEWIRE HAVING DISTALLY LOCATED MARKER SEGMENT

[75] Inventor: Fernando M. Viera, Hialeah, Fla.

[73] Assignee: Cordis Corporation, Miami Lakes, Fla.

[21] Appl. No.: 65,453

[22] Filed: May 21, 1993

Related U.S. Application Data

[63] Continuation of Ser. No. 845,551, Mar. 4, 1992, abandoned.

[51] Int. Cl.$^5$ ................................................ A61B 5/00
[52] U.S. Cl. .................................. 128/772; 128/657; 604/164; 604/282
[58] Field of Search ................... 128/772, 657, 658; 604/95, 164, 280, 282; 606/192

[56] References Cited

U.S. PATENT DOCUMENTS

| | | | |
|---|---|---|---|
| 4,538,622 | 9/1985 | Samson et al. | 128/772 |
| 4,721,117 | 1/1988 | Mar et al. | 128/772 |
| 4,748,986 | 6/1988 | Morrison et al. | 128/772 |
| 4,763,647 | 8/1988 | Gambale | 128/657 |
| 4,813,434 | 3/1989 | Buchbinder et al. | 128/772 |
| 4,821,722 | 4/1989 | Miller et al. | 604/96 |
| 4,922,924 | 5/1990 | Gambale et al. | 128/772 |
| 5,063,935 | 11/1991 | Gambale | 128/657 |
| 5,174,302 | 12/1992 | Palmer | 128/772 |
| 5,211,636 | 5/1993 | Mische | 604/264 |
| 5,228,453 | 7/1993 | Sepetka | 128/772 |
| 5,253,653 | 10/1993 | Daigle et al. | 128/772 |

FOREIGN PATENT DOCUMENTS

| | | | |
|---|---|---|---|
| 2180277 | 7/1990 | Japan | 128/772 |
| 9100051 | 1/1991 | PCT Int'l Appl. | 128/772 |
| 9114395 | 10/1991 | PCT Int'l Appl. | 128/772 |

*Primary Examiner*—Stephen C. Pellegrino
*Assistant Examiner*—Guy V. Tucker
*Attorney, Agent, or Firm*—Watts, Hoffmann, Fisher & Heinke

[57] ABSTRACT

A flexible guidewire having a marker region at its distal end. The marker region is defined by spaced apart platinum bands attached to a reduced diameter portion of a guidewire core wire. A flexible spring overlies the marker region and is of a two-piece construction. A proximal end of the spring is constructed of stainless steel that has multiple spaced gaps to facilitate viewing of the platinum bands. A distal portion of the spring is constructed of platinum and is welded to a distal end of the core wire.

9 Claims, 2 Drawing Sheets

GUIDEWIRE HAVING DISTALLY LOCATED MARKER SEGMENT

This application is a continuation of application Ser. No. 07/845,551, filed Mar. 4, 1992, now abandoned.

TECHNICAL FIELD

The present invention relates to a flexible elongated guidewire used to position a catheter within a subject and more particularly concerns a guidewire having a marker segment at its distal end.

BACKGROUND ART

Percutaneous Coronary Angioplasty is a therapeutic medical procedure that can increase blood flow through the coronary artery. It can sometimes be used as an alternative to coronary by-pass surgery. A catheter having a deflated balloon at its distal end is guided through a patient's cardiovascular system to the coronary artery of the heart. The balloon is inflated to compress deposits that have accumulated along the inner walls of the coronary artery to widen the artery lumen and increase blood flow.

A known technique for positioning the catheter balloon employs an elongated flexible guidewire that is inserted into the patient and used to guide the catheter into the patient.

The guidewire distal tip follows a tortuous or winding path as it is inserted into the subject. The distal tip is flexible to avoid damaging inner walls of the blood vessels that the guidewire tip contacts along the winding path. The distal tip is often pre-bent to a desired configuration so that the guidewire can be inserted into the branching blood vessels along the path. When the tip is pre-bent the physician must be able to orient the tip so it can be pushed into these branching blood vessels.

Representative prior art patents that disclose flexible, elongated guidewires are U.S. Pat. No. 4,545,390 to Leary, U.S. Pat. No. 4,538,622 to Samson et al. and U.S. Pat. No. 3,906,938 to Fleischhacker. U.S. Pat. 4,846,186 to Box et al. is assigned to the assignee of the present application and is incorporated herein by reference.

One problem with currently available guidewires concerns the visibility of the guidewire. If the guidewire is fully opaque on a viewing screen, it can hinder viewing of post angioplasty angiograms used in studying the effects the angioplasty procedure had on the treated vessel. Guidewires that have only an opaque tip do not adequately depict the arterial path on the viewing monitor.

U.S. Pat. No. 4,922,924 to Gambale et al. concerns a guidewire for use with a catheter. The guidewire includes a coil assembly that is formed from a highly radiopaque coil and a non-radiopaque coil, arranged in bifilar arrangement to define a moderate radiopacity guidewire section.

DISCLOSURE OF THE INVENTION

The present invention relates to an elongated flexible guidewire designed for insertion into blood vessels to aid in positioning a catheter within a subject.

An elongated flexible guidewire constructed in accordance with the invention includes a core wire having a first diameter portion extending to a distal portion of the guidewire where the core wire tapers to a second, lesser diameter portion shorter than said first diameter portion. A flexible coiled wire spring is attached at either of its ends to the core wire. Highly radiopaque marker bands are spaced along the lesser diameter of the core wire to increase the visibility of the guidewire at the guidewire's distal end.

In accordance with a preferred construction the flexible coil spring is constructed from two segments having different radiopacity. A stainless steel segment extends over the highly radiopaque marker bands that are spaced along the core wire. The stainless steel segment is connected to a highly radiopaque platinum coil spring segment that is visible when viewed on an X-ray viewing monitor.

As the stainless steel segment is wound, the pitch of the winding is altered to leave gaps between adjacent coils at specified locations. The highly opaque marker bands are visible beneath these gaps.

From the above it is appreciated that one object of the invention is a flexible guidewire having improved visibility due to its banded distal construction. This and other objects, advantages and features of the invention will become better understood from a detailed description of the invention which is described in conjunction with the accompanying drawings.

BEST MODE FOR CARRYING OUT THE INVENTION

Figures 1, 3:
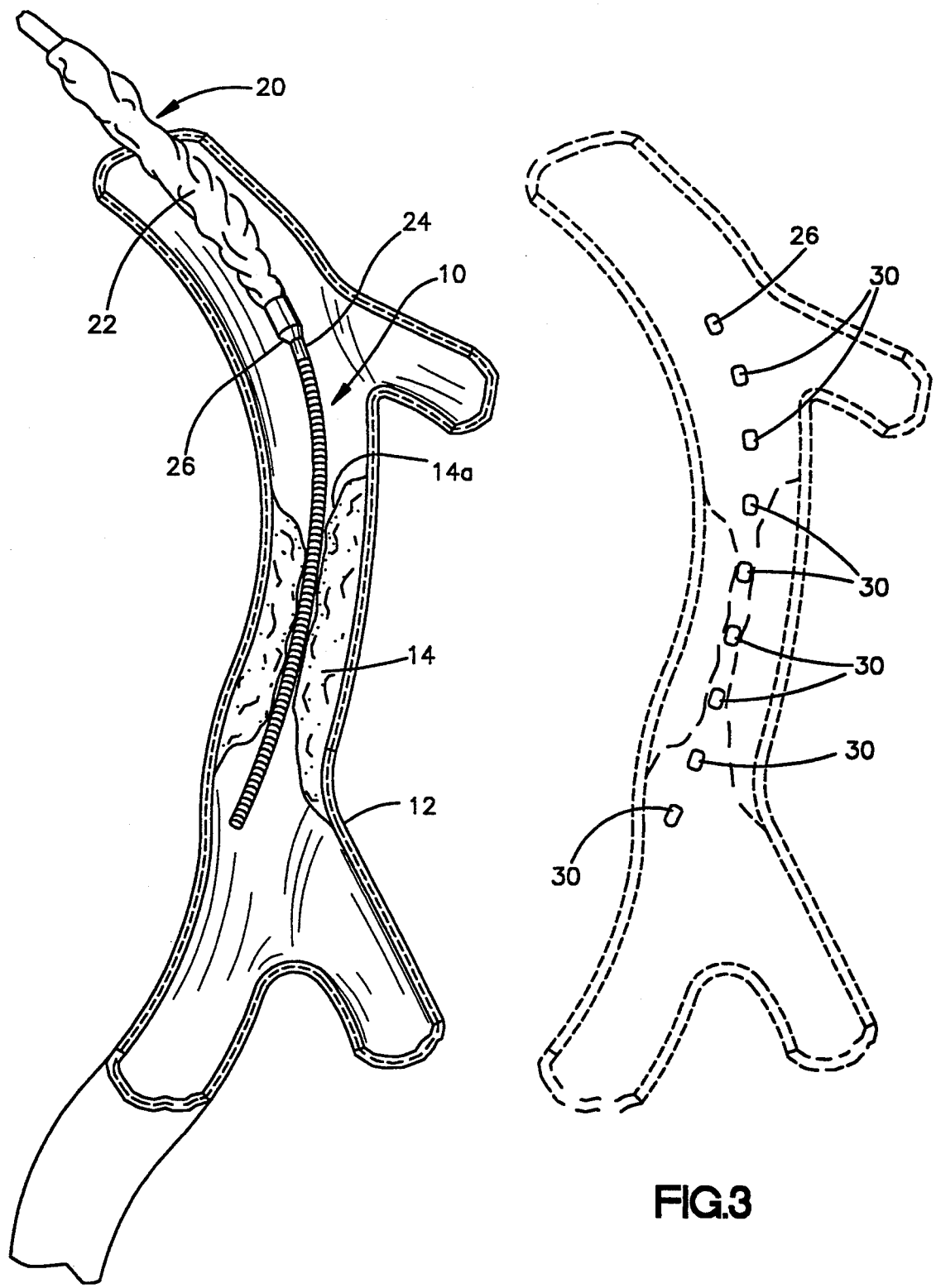
FIG. 1 is a diagrammatic view showing a blood vessel that has been occluded with deposits along an inner wall and shows the positioning of a flexible guidewire within the blood vessel.
FIG. 3 is a view of a flexible guidewire constructed in accordance with the invention as it appears when viewed on a fluoroscopic examining screen.

Turning now to the drawings, FIG. 1 illustrates a distal portion of a flexible, small diameter guidewire 10 that can be guided through a patient cardiovascular system. A distal end of the guidewire is shown in FIG. 1 approaching a region in a blood vessel 12 having occlusions 14 which restrict blood flow through the blood vessel 12. The guidewire 10 is long enough to be routed from a patient entry point through the patient to the obstructed blood vessel region. In a preferred embodiment the guidewire has a length L of 175 cm. (approximately 69 inches). As the guidewire 10 is inserted along the tortuous path to the obstructed blood vessel region, an attending physician conducting the procedure monitors progress of the guidewire 10 on a viewing screen.

The FIG. 1 depiction illustrates use of a guidewire for routing a balloon catheter 20 to the vicinity of the obstructions 14. The balloon catheter 20 includes a passageway or lumen that extends from a proximal location outside the patient to a distally located balloon 22. Fluid is routed into the catheter through this lumen to inflate the balloon 22. A distal tip portion 24 of the catheter 20 includes a marker band 26 to aid the attending physician in monitoring balloon catheter progress as it is positioned within the patient. A second, center passageway or lumen in the catheter 20 has a diameter sufficient to accommodate the guidewire 10 so that once the guidewire is properly positioned within the subject, the catheter 20 can be slid over the guidewire.

The distal tip portion of the guidewire 10 is flexible and can be bent to a predetermined configuration to facilitate routing the guidewire 10 along the cardiovascular system to the FIG. 1 region of the blood vessel 12. The pre-bent tip can be re-oriented by the physician. Torques applied to the proximal end of the guidewire are transmitted along the length of the guidewire and re-orient the distal tip to point in a desired direction.

In use, a distal end of the guidewire 10 is routed through a narrow passageway 14a in the obstruction 14 and the balloon catheter 20 slipped over the guidewire until the balloon 22 bridges the region 14 of obstructions within the blood vessel 12. The balloon 22 is then inflated and the balloon's outer surface contacts the obstruction 14. The inner walls of the obstruction 14 are compressed and a wider lumen or passageway created in the blood vessel 12.

As described in detail below, the guidewire 10 is constructed so that bands or regions 30 (FIG. 3) of high radiopaqueness appear when the blood vessel 12 is monitored on a viewing screen. The bands 30 are separated at a fixed distance thereby giving a reference length. The opacity of the bands 30 can be varied and in such an embodiment, the opacity of the bands 30 diminishes at the distal or working end of the guidewire 10. This would allow adequate tracing of the guidewire while minimizing interference with a post procedure angiogram.

Figure 2:
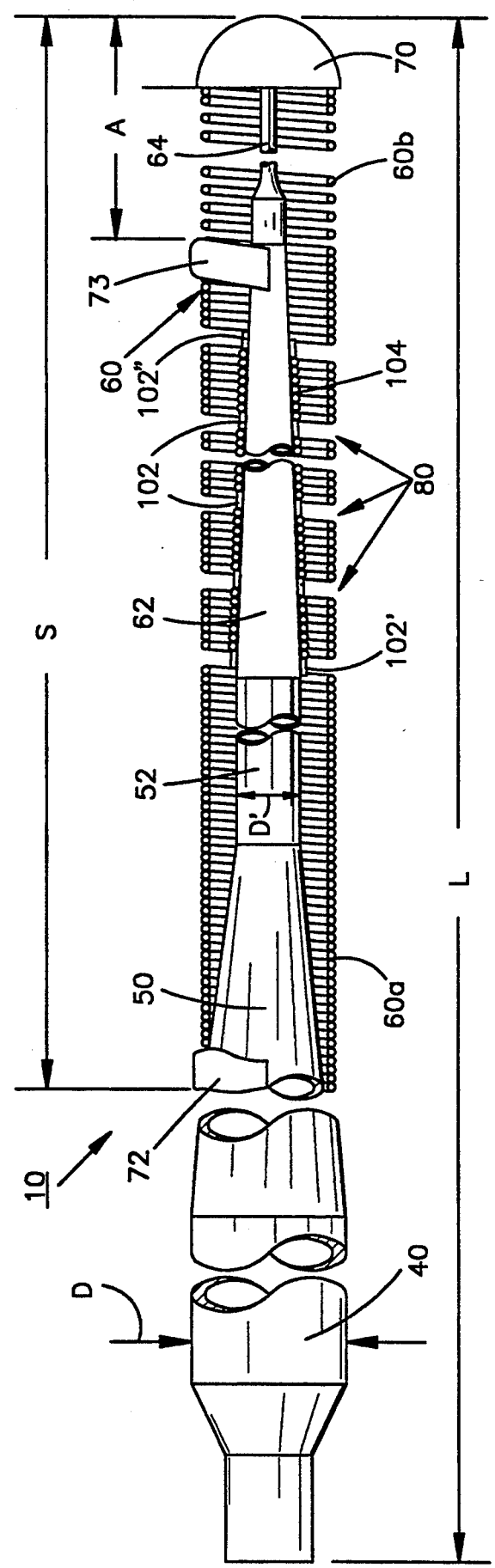
FIG. 2 is an elevation segmented view of a flexible guidewire core wire constructed in accordance with the invention.

Turning now to FIG. 2, the guidewire 10 is seen to include a center stainless steel wire core 40 having a first uniform diameter D, in the range 0.0130-0.035 inch, extending well over half the length "L" of the guidewire. To improve the depiction of details of the distal portion of the guidewire 10, this uniform diameter elongated portion has been sectioned and a major portion of its length deleted from FIG. 2.

The total length of the uniform diameter portion 40 is approximately 148 cm. of the total guidewire length of 175 cm. It is typically covered with a suitable coating to make its outer surface lubricious. A short proximal portion of the core 40 is exposed. The remaining distal segment of the guidewire has a length S of approximately 27 cm.

At the guidewire's distal end, the wire core 40 tapers along a portion 50 uniformly to a portion 52 having a uniform diameter D'. A coiled wire spring 60 covers a distal portion of the core wire. A first portion 60a of the spring 60 is constructed of a low radiopaque wire having a thickness of 0.0025-0.004 inches and is attached to the tapered center core portion 50. The core 40 again tapers uniformly along a segment 62. An extreme distal segment 64 of the core 40 is flattened and surrounded by a second less tightly coiled portion 60b of the spring 60 constructed from a radiopaque wire having the same thickness as the wire that forms the first portion 60a. This distal segment of the guidewire 10 has a length A of approximately 1 inch and can be pre-bent to a particular configuration by the attending physician to facilitate insertion of the guidewire within the subject.

At the extreme distal tip portion of the guidewire 10, a weld 70 attaches the distal portion 60b of the spring 60 to the flattened portion 64 of the core. The weld defines a smooth hemispherical bead which does not damage the inner lining of the blood vessels as the guidewire tip comes in contact with those linings.

The spring 60 is soldered to the core 40 using Low Temperature, Surgical Grade Solder. One solder connection 72 joins the proximal spring portion 60a and the tapered portion 50. A second solder connection 73 joins both spring portions 60a, 60b to the core wire at the small diameter end of the tapered core segment 62. The core 40 is constructed from a uniform diameter stainless steel wire which is centerless ground along the tapered segment 50 to the reduced diameter segment 52 and again ground along the tapered segment 62. The flattened portion 64 is formed by rolling or stamping a uniform diameter core portion having an initial diameter of 0.0025 inch which when flattened by a die, results in 0.0018 inch thick by 0.0045 inch wide flattened portion that "bulges" outward on two sides.

The spring 60 is closely packed along the tapered core portion 50 and uniform diameter portion 52 so that adjacent coils of the spring 60 touch each other. The coils of the spring portion 60a are less tightly packed at fixed distances to define gaps or spaces 80. These gaps 80 overlie multiple high radiopaque bands or rings 102 separated by stainless steel coil segments 104. The bands 102 are preferably platinum metal and are spaced apart a fixed distance and provide a length reference for a physician viewing the core wire 10 on a viewing screen. Each band 102 on the core wire corresponds to a band 30 on the viewing screen depicted in FIG. 3.

During fabrication of the guidewire 10, a first proximal band 102' is slipped over the core wire and attached by soldering to the core wire. Multiple coil segments 104 and bands 102 are then alternated along a length of the core wire. A final distal band 102" is slipped over the core wire and soldered to the core wire. The separation between bands 102 can be adjusted depending upon the intended use of the guidewire. In a preferred embodiment, the separation is the same between adjacent bands and is determined by the number of coils in the coil segments 104. While several adjacent coils are depicted between adjacent bands 102 in FIG. 2, it is appreciated that many more coils would be used in fabricating the guidewire to achieve band spacing of approximately one-half inch. If it is desired to have the shades of the visible bands 30 lighter, a different alloy or material is utilized for different bands 102.

The guidewire 10 depicted in FIG. 2 is particularly suited for insertion into small diameter blood vessels and can be used, for example, for positioning a balloon in a bridging relationship within the coronary artery.

FIG. 3 illustrates the image of the guidewire 10 which a physician would see while using the guidewire during angioplasty. Unlike a fully radiopaque guidewire, the seven bands 30 are visible at spaced locations to aid the physician during the angioplasty while not interfering with a post procedure angiogram. The bands 30 are equally spaced at one-half inch intervals to provide a reference for the physician with regard to positioning the guidewire 10 within the blood vessel 12.

The dimensions mentioned in this specification are for a preferred embodiment in the invention for use in small diameter blood vessels. These dimensions are representative of this use and are not intended to limit the invention, but rather define a small diameter guidewire whose characteristics are particularly advantageous. It is the intent, however, that the invention include all modifications and/or alterations from the disclosed dimensions and design falling within the spirit or scope of the appended claims.

I claim:

1. A guidewire for insertion into a subject comprising:

a) an elongated core wire having a first, uniform diameter portion and a second reduced diameter portion at a distal end of the elongated core wire;

b) a marker member attached to the second reduced diameter portion of the core wire comprising a first, proximal highly radiopaque marker band attached to the core wire and multiple additional highly radiopaque marker bands on the core wire spaced from each other by coiled wire segments on the core wire of less radiopaque material and including a distal marker band attached to the core wire; and c) a spring member constructed of multiple coils of wire overlying the marker member and attached to the core wire at connection regions distal and proximal to the marker member;

d) whereby each of said marker bands appears as a distinct band when viewed on a radiographic viewing screen outside the subject.

2. The guidewire of claim 1 where the spring member comprises a distal highly radiopaque portion and a proximal less radiopaque portion.

3. The guidewire of claim 1 where the spring member comprises multiple regions of tightly wound coil segments spaced apart by multiple loosely wound regions, said loosely wound regions aligned with said marker bands to enhance the distinctness of the marker bands when viewed on the radiographic viewing screen.

4. A guidewire for insertion into a subject comprising:

a) an elongated core wire having a first, uniform diameter portion and a second reduced diameter portion at a distal end of the elongated core wire;

b) a plurality of individual highly radiopaque marker bands attached to and axially supported by the second reduced diameter portion of the core wire at spaced apart intervals, whereby each of said marker bands appear as a distinct band when viewed on a radiographic viewing screen outside the subject; and c) a spring member constructed of multiple coils of wire overlying the marker bands and attached to the core wire at connection regions distal and proximal to the marker bands;

d) the spring member including loosely wound regions at the longitudinal location of the marker bands to enhance a distinctness of the marker bands when viewed on the radiographic viewing screen.

5. The guidewire of claim 4 where the spring member comprises a first low radiopaque segment and a second high radiopaque segment attached to the core wire by a generally hemispherical weld.

6. The guidewire of claim 4 additionally comprising individual coiled wire segments supported by the reduced diameter portion of the core wire that are interposed between the marker bands.

7. The guidewire of claim 6 where the coiled wire segments consist of stainless steel and the marker bands consist of platinum bands.

8. A guidewire for insertion into a subject comprising:

a) an elongated core wire having a first, uniform diameter portion and a second reduced diameter portion at a distal end of the elongated core wire;

b) a marker member having a proximal and a distal end attached to the second reduced diameter portion of the core wire comprising a plurality of individual, highly radiopaque marker bands spaced apart along the reduced diameter portion of said elongated core wire, whereby each of said marker bands appears as a distinct band when viewed on a radiopaque viewing screen outside the subject; and c) a spring member constructed of multiple coils of wire overlying the marker member and attached to the core wire at connection regions distal and proximal to the marker member and including multiple regions of tightly wound coil segments spaced apart by multiple loosely wound regions aligned with the marker bands of the marker member to enhance a distinctness of the marker bands when viewed on the radiopaque viewing screen.

9. The guidewire of claim 8 where the marker member additionally comprises individual coiled wire segments comprising a less radiopaque material that are interposed between the individual marker bands.

* * * * *